(12) United States Patent
Hatcher et al.

(10) Patent No.: US 11,904,107 B2
(45) Date of Patent: Feb. 20, 2024

(54) POLYMER COATED WIRES FOR REINFORCED CATHETER SYSTEMS

(71) Applicant: Switchback Medical LLC, Maple Grove, MN (US)

(72) Inventors: Brady Hatcher, Rogers, MN (US); Randy Beyreis, Corcoran, MN (US); Brett Allyn Williams, North Oaks, MN (US)

(73) Assignee: LightningCath, Inc., Maple Grove, MN (US)

( * ) Notice: Subject to any disclaimer, the term of this patent is extended or adjusted under 35 U.S.C. 154(b) by 777 days.

(21) Appl. No.: 16/982,012

(22) PCT Filed: Mar. 11, 2019

(86) PCT No.: PCT/US2019/021676
§ 371 (c)(1),
(2) Date: Sep. 17, 2020

(87) PCT Pub. No.: WO2019/182791
PCT Pub. Date: Sep. 26, 2019

(65) Prior Publication Data
US 2021/0016057 A1 Jan. 21, 2021

Related U.S. Application Data

(60) Provisional application No. 62/645,692, filed on Mar. 20, 2018.

(51) Int. Cl.
*A61M 25/00* (2006.01)

(52) U.S. Cl.
CPC ... *A61M 25/005* (2013.01); *A61M 2025/0058* (2013.01); *A61M 2025/0063* (2013.01)

(58) Field of Classification Search
CPC ........ A61M 25/005; A61M 2025/0058; A61M 2025/0063; A61M 25/0012; A61M 25/0043; A61M 25/0009; A61M 25/0045
See application file for complete search history.

(56) References Cited

U.S. PATENT DOCUMENTS 2,322,756 A   6/1943   Wallder
5,667,499 A   9/1997   Welch
(Continued)

FOREIGN PATENT DOCUMENTS

CA    2812987 A1       3/2012
JP    2016172180 A  *  9/2016
(Continued)

OTHER PUBLICATIONS

PCT International Search Report and Written Opinion in International Application No. PCT/US2019/021676, dated May 24, 2019, 8 pages.

(Continued)

*Primary Examiner* — Jason E Flick
(74) *Attorney, Agent, or Firm* — Gallium Law; Wesley Schwie; Justin Schwechter

(57) ABSTRACT

The disclosure describes a reinforced catheter system, such as a wire, that includes an inner layer having an inner lumen configured to allow an object to slideably move within the inner lumen. The catheter system may include a reinforcement structure, having an outer coating, such as a polymer. The reinforcement structure may be coupled over the inner layer to thereby at least partially encapsulate the inner layer. The catheter system may include an outer surface coupled over the reinforcement structure and the inner layer to thereby encapsulate both the inner layer and the reinforcement structure. The outer coating of the reinforcement structure may be re-flowed to thereby bond the inner layer (Continued)

to the outer surface to thereby create a reinforced homogeneous structure.

20 Claims, 4 Drawing Sheets

(56) References Cited

U.S. PATENT DOCUMENTS

| | | | |
|---|---|---|---|
| 5,836,925 | A | 11/1998 | Soltesz |
| 6,030,371 | A | 2/2000 | Pursley |
| 6,143,013 | A | 11/2000 | Samson |
| 6,213,995 | B1 | 4/2001 | Steen |
| 6,562,022 | B2 | 5/2003 | Hoste |
| 6,635,047 | B2 | 10/2003 | Forsberg |
| 6,669,886 | B1 | 12/2003 | Willard |
| 6,942,654 | B1 | 9/2005 | Schaefer |
| 7,000,305 | B2 | 2/2006 | Jayaraman |
| 7,112,298 | B2 | 9/2006 | Kampa |
| 7,507,229 | B2 | 3/2009 | Hewitt |
| 7,597,830 | B2 | 10/2009 | Zhou |
| 7,615,043 | B2 | 11/2009 | Zhou |
| 7,713,259 | B2 | 5/2010 | Gosiengfiao |
| 7,828,793 | B2 | 11/2010 | Thompson |
| 7,955,313 | B2 | 6/2011 | Boismier |
| 8,142,415 | B2 | 3/2012 | Warnock |
| 8,206,373 | B2 | 6/2012 | Zhou |
| 8,251,976 | B2 | 8/2012 | Zhou |
| 8,431,057 | B2 | 4/2013 | Guo |
| 8,465,469 | B2 | 6/2013 | Brightbill |
| 8,475,431 | B2 | 7/2013 | Howat |
| 8,864,744 | B2 | 10/2014 | Howat |
| 9,060,785 | B2 | 6/2015 | Howat |
| 2002/0132076 | A1 | 9/2002 | Stevens |
| 2006/0242824 | A1 | 11/2006 | Varkey |
| 2009/0069748 | A1* | 3/2009 | Schaeffer .......... A61M 25/1006 604/103.09 |
| 2014/0110147 | A1 | 4/2014 | Elie |
| 2016/0136387 | A1* | 5/2016 | Otake ............... A61M 25/0012 604/526 |

FOREIGN PATENT DOCUMENTS

| | | |
|---|---|---|
| JP | 2016172180 A | 9/2016 |
| WO | 1997036629 A1 | 10/1997 |

OTHER PUBLICATIONS

PCT International Preliminary Report on Patentability in International Application No. PCT/US2019/021676, dated Sep. 22, 2020, 7 pages.

* cited by examiner

POLYMER COATED WIRES FOR REINFORCED CATHETER SYSTEMS

CROSS-REFERENCE TO RELATED APPLICATIONS

This application claims the benefit and priority of U.S. Provisional Patent Application No. 62/645,692; filed Mar. 20, 2018; and entitled POLYMER COATED WIRES FOR REINFORCED CATHETER SYSTEMS; the entire contents of which are incorporated herein by reference.

This application claims the benefit and priority of International Application No. PCT/US2019/021676; filed Mar. 11, 2019 with the U.S. Patent and Trademark Office; and entitled POLYMER COATED WIRES FOR REINFORCED CATHETER SYSTEMS; the entire contents of which are incorporated herein by reference.

BACKGROUND

Field of Invention

The present invention relates to wires and more specifically to polymer coated wires for reinforced catheter systems.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments.

DETAILED DESCRIPTION

Figure 1:
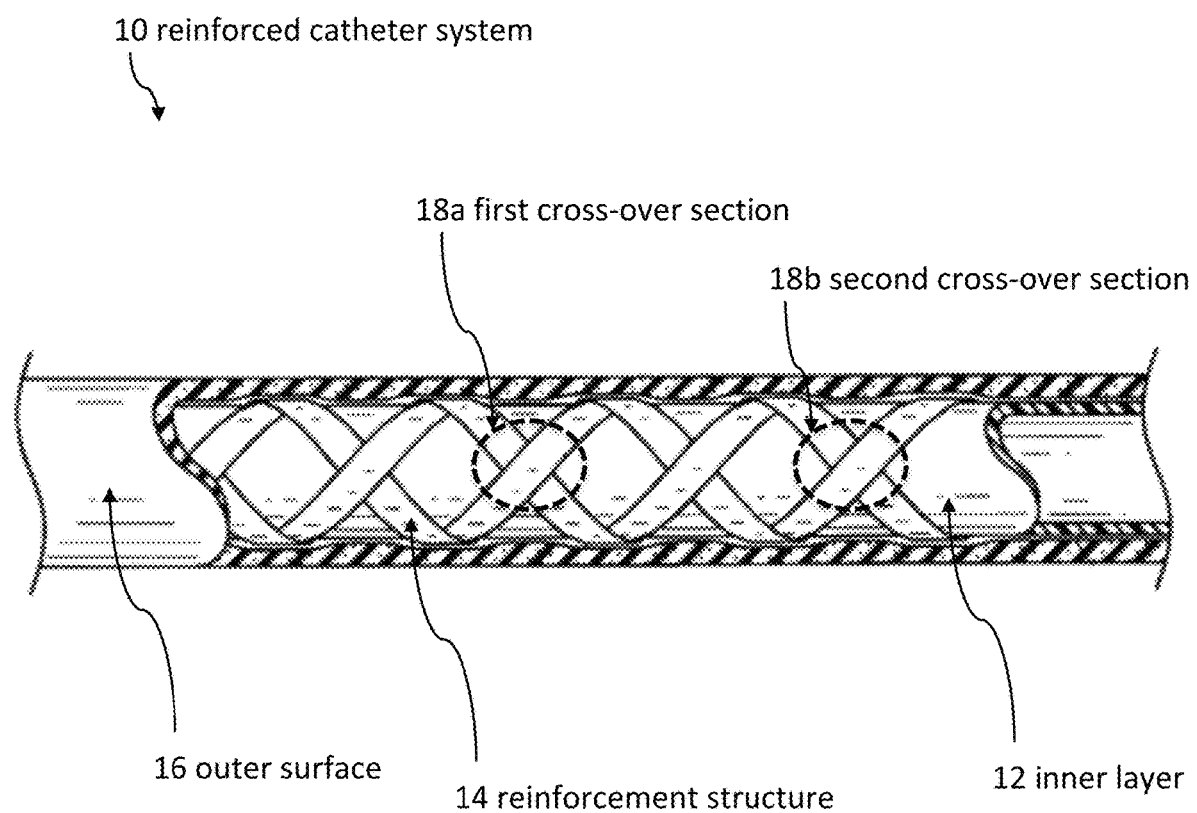
FIG. 1 illustrates a reinforced catheter system, according to some embodiments.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Additionally, reference is made to the accompanying drawings that form a part hereof, and in which the specific embodiments that may be practiced is shown by way of illustration. These embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

Problem

Currently, reinforced structures (e.g. flat or round metal wires) do not allow the outer polymer material of a reinforced medical catheter to re-flow and fully encapsulate the reinforcing structure. The material is not able to flow under the crossover sections or under the structure to adhere to the liner material.

Idea

To polymer coat substrates, which may be indented, to be used as a reinforcement structures for medical catheters.

Solution

Polymer coat the outside surface area of the reinforcement material to facilitate adhesion at the crossover sections to adhere the inner layer to the outer surface and lock the structure in place.

Benefit

Locking the crossover sections will improve torque and promote adhesion of the outer polymer layer of the catheter to the inner layer (e.g. liner) thereby encapsulating and adhering all of the components together making a homogeneous structure without gaps.

Current Manufacturing Process for Reinforced Catheters

1. The inner layer/liner is stretched over a process mandrel to maintain the inside diameter of the inner lumen of the catheter.
2. Once the inner layer/liner is stretched onto the mandrel it is placed into a braider or coil winder to apply the reinforcement structure.
3. After the reinforcement structure is applied the subassembly is removed from the braider or coil winder.
4. Once removed from the braider or coil winder the outer layer is loaded over the subassembly. The outer layer may consist of several segments/durometers of extrusions.
5. After the outer layer is loaded onto the subassembly a tube of heat shrink is loaded over the entire subassembly and then placed into a reflow oven to melt the outer layer down onto the inner layer/reinforcement subassembly.
6. Once the reflow cycle is completed the subassembly is removed from the oven and the heat shrink is removed from the catheter Process mandrel: 304SST rod or hypotube, and/or PTFE beading.

Outer layer material: All grades of Pebax, Nylon, Urethane, HDPE, and/or LDPE.

Inner layer materials: Etched PTFE, HDPE, LDPE, Kynar, all grades of Pebax, nylon, and/or urethane.

Reinforcement materials: 304, 316SST, MP35N, Tungsten, Kevlar, PEEK, LCP, polyimide, and/or nylon.

Heat shrink: FEP, PTFE, and/or polyolefin.

Future Manufacturing Process for Reinforced Catheters

This disclosure proposes manufacturing catheters with a reinforcement material having a thin polymer film coating on the outside surface of the reinforcement material to promote adhesion to the outer and inner layer and to itself at the crossover sections.

LIST OF REFERENCE NUMERALS

10—Reinforced catheter system
12—Inner layer
14—Reinforcement structure
16—Outer surface
18a—First crossover section
18b—Second crossover section System (Wire) Embodiments FIG. 1 illustrates a reinforced catheter system 10 embodiment having a thin polymer film coating as discussed above. According to FIG. 1, the reinforced catheter system 10 includes an inner layer 12 having an inner lumen configured to allow an object (e.g. a stylet) to slideably move within the inner lumen. The system 10 can include a reinforcement structure 14 coupled over the inner layer 12 to thereby at least partially encapsulate the inner layer 12. The system 10 may also include an outer surface 16 coupled over the reinforcement structure 14 and the inner layer 12 to thereby encapsulate both the inner layer 12 and the reinforcement structure 14. The outer surface 16 may include an outer layer coupled over the reinforcement structure 14 and the inner layer 12 to thereby encapsulate both the inner layer 12 and the reinforcement structure 14.

In order to reinforce the catheter system 10, the reinforcement structure 14 may include an outer coating, such as a polymer. The outer coating 14 may be bonded (e.g. adhesively bonded, chemical bonded, and the like) to an outside surface of the inner layer 12 and an inside surface of the outer layer 16 to thereby create a homogeneous structure. The outer coating and/or outer layer may include an extrusion coating and/or a dispersion coating.

In some embodiments, a first portion of the reinforcement structure 14a crosses over a second portion of the reinforcement structure 14b to thereby form a first crossover section 18. The outer coating may be arranged and configured to flow between the first portion 14a and the second portion 14b at the first crossover section 18. Therefore, the outer coating may bond the first portion 14a to the second portion 14b at the first crossover section 18. Furthermore, in some embodiments, the outer coating is arranged and configured to bond to the inner layer, the reinforcement structure, and the outer layer together to form a homogeneous laminated structure.

The components of the system 10 may comprise any type of material. For example, the inner layer 12, outer coating, and/or outer layer may include and/or be constructed of any combination of etched polytetrafluoroethylene (PTFE), high-density polyethylene (HDPE), low-density polyethylene (LDPE), polyvinylidene fluoride (Kynar), polyether block amide (Pebax), nylon, urethane, polyether ether ketone (PEEK), liquid crystal polymer (LCP), and/or polyimide. The reinforcement structure 14 may include and/or be constructed of any combination of 304 stainless steel, 316 stainless steel, MP35N®, Kevlar®, tungsten, polyether ether ketone (PEEK), Ultra-high-molecular-weight polyethylene (UHMWPE), and/or polyimide.

In some embodiments, the system 10 includes a removable heat shrink layer coupled to the outer layer whereby the removable heat shrink layer fully encapsulates the inner layer, reinforcement structure, outer coating, and outer layer. The removable heat shrink may include fluorinated ethylene propylene (FEP), polytetrafluoroethylene (PTFE), and/or polyolefin.

Figure 2:
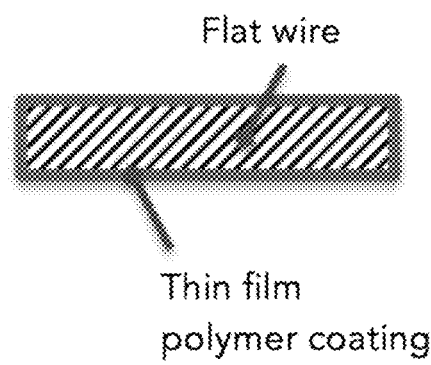
FIG. 2 illustrates various wire shapes and types, according to some embodiments.
Figure 2:
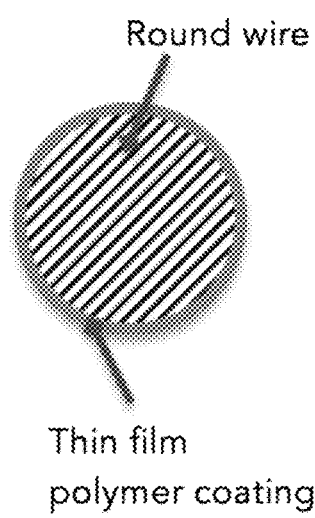
Figure 2:
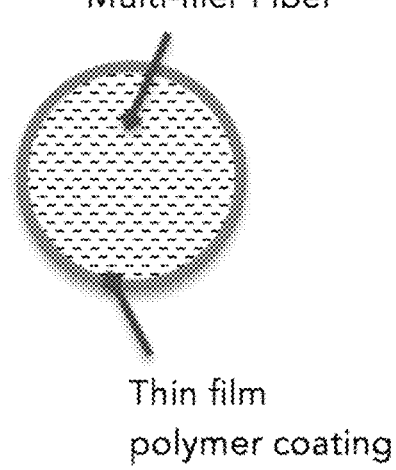
Figure 3:
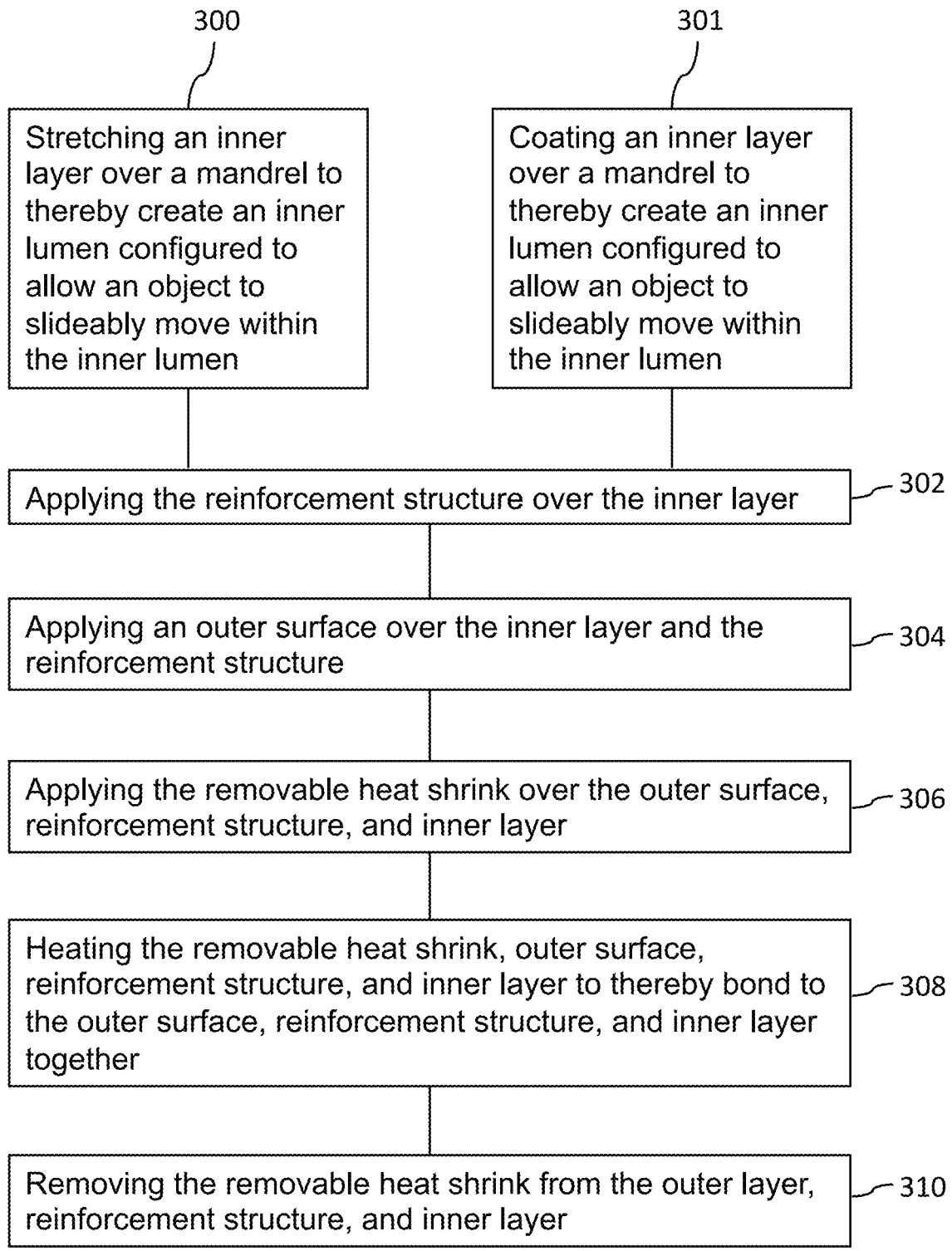
FIG. 3 illustrates a flow chart of method steps for manufacturing reinforced catheter systems, according to some embodiments.

As further shown in FIG. 2, the system 10 may define a wire having a variety of shapes. For example, the wire may define a flat wire or a round wire. In some embodiments, the wire defines a multi-filer fiber.

Method Embodiments

The disclosure also includes methods of manufacturing a reinforced catheter 10 having an inner layer 12, a reinforcement structure 14 comprising an outer surface, and a removable heat shrink. Methods may include stretching the inner layer 12 over at least one of a wire and a mandrel to thereby create an inner lumen configured to allow an object (e.g. stylet) to slideably move within the inner lumen (at step 300). Alternatively, methods may include coating an inner layer over at least one of a wire and a mandrel to thereby create an inner lumen configured to allow an object to slideably move within the inner lumen (at step 301).

In some embodiments, the method includes applying the reinforcement structure 14 over the inner layer 12 (at step 302) and applying the outer surface 16 over the inner layer 12 and the reinforcement structure 14 (at step 304). Applying the reinforcement structure 14 over the inner layer may include placing the inner layer into a braider and/or coil winder to apply the reinforcement structure 14.

Methods may also include applying the removable heat shrink over the outer surface 16, reinforcement structure 14, and inner layer 12 (at step 306). Additionally, methods may include heating the removable heat shrink, outer surface 16, reinforcement structure 14, and inner layer 12 to thereby bond to the outer surface 16, reinforcement structure 14, and inner layer 12 together (at step 308). Methods may even include removing the removable heat shrink from the outer layer 16, reinforcement structure 14, and inner layer 12 (at step 310).

Figure 4:
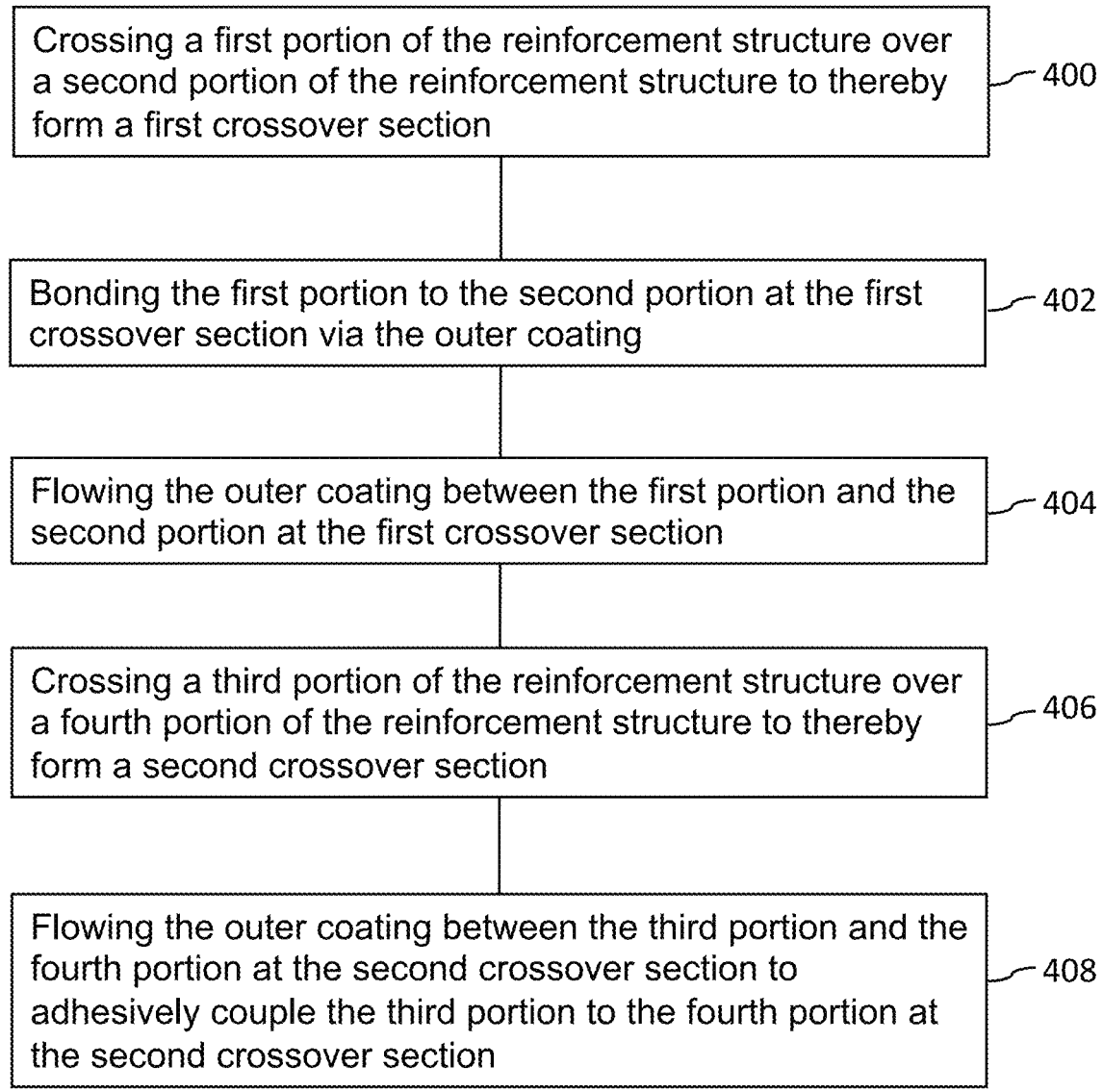
FIG. 4 illustrates a flow chart of additional method steps for manufacturing reinforced catheter systems, according to some embodiments.

Now with reference to FIG. 4, in order to reinforce the catheter system 10, methods may also include crossing a first portion of the reinforcement structure 14a over a second portion of the reinforcement structure 14b to thereby form a first crossover section 18 (at step 400). Methods may include bonding the first portion 14a to the second portion 14b at the first crossover section 18a via the outer coating (at step 402). Methods may further include flowing the outer coating between the first portion 14a and the second portion 14b at the first crossover section 18 (at step 404).

In some embodiments, the method includes crossing a third portion of the reinforcement structure 14c over a fourth portion of the reinforcement structure 14d to thereby form a second crossover section 18b (at step 406). Accordingly, methods may include flowing the outer coating between the third portion 14c and the fourth portion 14d at the second crossover section 18b to adhesively couple the third portion 14c to the fourth portion 14d at the second crossover section 18b (at step 408).

Furthermore, methods may include heating the removable heat shrink, outer layer, reinforcement structure, and inner layer in a heating apparatus, such as an oven, a reflow oven, and/or a thermal bonder. It should be appreciated that any of the steps disclosed herein, such as the applying steps, may be performed automatically by a machine, manually by a person, or some combination of the two.

Interpretation

The term "approximately" means that something is almost, but not completely, accurate or exact; roughly. Additionally, the term "substantially" means to a great or significant extent; for the most part, essentially.

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

Some of the devices, systems, embodiments, and processes use computers. Each of the routines, processes, methods, and algorithms described in the preceding sections may be embodied in, and fully or partially automated by, code modules executed by one or more computers, computer processors, or machines configured to execute computer instructions. The code modules may be stored on any type of non-transitory computer-readable storage medium or tangible computer storage device, such as hard drives, solid state memory, flash memory, optical disc, and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments include A, B, and C. The term "and/or" is used to avoid unnecessary redundancy.

Although the embodiments herein are described with various specific embodiments, it will be obvious for a person skilled in the art to practice the invention with modifications. However, all such modifications are deemed to be within the scope of the claims. While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

Furthermore, the foregoing description of the specific embodiments will so fully reveal the general nature of the embodiments herein that others can, by applying current knowledge, readily modify and/or adapt for various applications such specific embodiments without departing from the generic concept, and, therefore, such adaptations and The following is claimed:

1. A reinforced catheter system, comprising:
   an inner layer having an inner lumen configured to allow an object to slideably move within the inner lumen;
   a reinforcement structure coupled over the inner layer to thereby at least partially encapsulate the inner layer;
   an outer layer coupled over the reinforcement structure and the inner layer to thereby encapsulate both the inner layer and the reinforcement structure; and
   a film coating chemically bonded to the reinforcement structure, wherein the film coating is chemically bonded to an outside surface of the inner layer and an inside surface of the outer layer.

2. The reinforced catheter system of claim 1, wherein the outer layer comprises at least one of an extrusion coating and a dispersion coating.

3. The reinforced catheter system of claim 1, wherein the film coating comprises at least one of an extrusion coating and a dispersion coating.

4. The reinforced catheter system of claim 1, wherein a first portion of the reinforcement structure crosses over a second portion of the reinforcement structure to thereby form a first crossover section.

5. The reinforced catheter system of claim 4, wherein the film coating bonds the first portion to the second portion at the first crossover section.

6. The reinforced catheter system of claim 5, wherein the film coating is bonded to the inner layer, reinforcement structure, and outer layer such that the inner layer, reinforcement structure, and outer layer form a homogeneous laminated structure.

7. The reinforced catheter system of claim 1, wherein the inner layer comprises at least one of etched polytetrafluoroethylene (PTFE), high-density polyethylene (HDPE), low-density polyethylene (LDPE), polyvinylidene fluoride, polyether block amide (Pebax), nylon, urethane, polyether ether ketone (PEEK), liquid crystal polymer (LCP), and polyimide.

8. The reinforced catheter system of claim 1, wherein the reinforcement structure comprises at least one of 304 stainless steel, 316 stainless steel, nickel-cobalt, aramid fiber, tungsten, polyether ether ketone (PEEK), Ultra-high-molecular-weight polyethylene (UHMWPE), and polyimide.

9. The reinforced catheter system of claim 1, wherein the film coating comprises at least one of etched polytetrafluoroethylene (PTFE), high-density polyethylene (HDPE), low-density polyethylene (LDPE), polyvinylidene fluoride, polyether block amide (Pebax), nylon, urethane, polyether ether ketone (PEEK), liquid crystal polymer (LCP), and polyimide.

10. The reinforced catheter system of claim 1, wherein the outer layer comprises at least one of etched polytetrafluoroethylene (PTFE), high-density polyethylene (HDPE), low-density polyethylene (LDPE), polyvinylidene fluoride, polyether block amide (Pebax), nylon, urethane, polyether ether ketone (PEEK), liquid crystal polymer (LCP), and polyimide.

11. The reinforced catheter system of claim 1, wherein the object comprises a stylet.

12. The reinforced catheter system of claim 1, wherein the reinforcement structure comprises a flat wire.

13. The reinforced catheter system of claim 1, wherein the reinforcement structure comprises a multi-filar fiber.

14. A reinforced catheter system, comprising:
   an inner layer having an inner lumen configured to allow an object to slideably move within the inner lumen;
   a reinforcement structure coupled over the inner layer to thereby at least partially encapsulate the inner layer;
   an outer layer coupled over the reinforcement structure and the inner layer to thereby encapsulate both the inner layer and the reinforcement structure; and
   a film coating adhesively bonded to the reinforcement structure, wherein the film coating is adhesively bonded to an outside surface of the inner layer and an inside surface of the outer layer.

15. The reinforced catheter system of claim 14, wherein the outer layer comprises at least one of an extrusion coating and a dispersion coating.

16. The reinforced catheter system of claim 14, wherein the film coating comprises at least one of an extrusion coating and a dispersion coating.

17. The reinforced catheter system of claim 14, wherein a first portion of the reinforcement structure crosses over a second portion of the reinforcement structure to thereby form a first crossover section.

18. The reinforced catheter system of claim 17, wherein the film coating bonds the first portion to the second portion at the first crossover section.

19. A reinforced catheter system, comprising:
   an inner layer having an inner lumen configured to allow an object to slideably move within the inner lumen;
   a reinforcement structure coupled over the inner layer to thereby at least partially encapsulate the inner layer,
      wherein a first portion of the reinforcement structure crosses over a second portion of the reinforcement structure to thereby form a first crossover section, and
      wherein the first portion of the reinforcement structure is selectively bonded to the second portion of the reinforcement structure at the first crossover section; and
   an outer layer coupled over the reinforcement structure and the inner layer to thereby encapsulate both the inner layer and the reinforcement structure.

20. The reinforced catheter system of claim 19, further comprising a film coating bonded to the reinforcement structure, wherein the film coating is bonded to an outside surface of the inner layer and an inside surface of the outer layer.

* * * * *